T 864,017

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED JULY 29, 1969

864 O.G. 1405

770,096

PROCESS FOR THE PREPARATION OF GLYCOL DIETHERS

Edward F. Sablatura, 207 Redwood St., and Nicholas B. Lorette, 512 Oak Drive, both of Lake Jackson, Tex. 77566

Filed Oct. 23, 1968. Published July 29, 1969
Int. Cl. C07c *41/10, 43/10*
U.S. Cl. 260—615
No Drawing. 8 Pages Specification

Glycol diethers are prepared by contacting a monoalkyl ether of an alkylene glycol or polyoxyalkylene glycol with a strong acid cation exchange resin in the hydrogen form at an elevated temperature.